United States Patent
Wong et al.

(10) Patent No.: US 9,700,285 B2
(45) Date of Patent: Jul. 11, 2017

(54) SPECTRAL DOPPLER IMAGING WITH INTERRUPTION AVOIDANCE

(71) Applicant: Siemens Medical Solutions USA, Inc., Malvern, PA (US)

(72) Inventors: King Yuen Wong, Issaquah, WA (US); Chi Hyung Seo, Sammamish, WA (US); Paul D. Freiburger, Seattle, WA (US)

(73) Assignee: Siemens Medical Solutions US, Inc., Malvern, PA (US)

( * ) Notice: Subject to any disclaimer, the term of this patent is extended or adjusted under 35 U.S.C. 154(b) by 127 days.

(21) Appl. No.: 14/788,137

(22) Filed: Jun. 30, 2015

(65) Prior Publication Data
US 2017/0000461 A1   Jan. 5, 2017

(51) Int. Cl.
| | |
|---|---|
| G06T 7/00 | (2006.01) |
| A61B 8/08 | (2006.01) |
| G06T 11/00 | (2006.01) |
| G06T 5/00 | (2006.01) |
| G01S 7/52 | (2006.01) |
| A61B 8/00 | (2006.01) |
| A61B 8/06 | (2006.01) |

(52) U.S. Cl.
CPC ............ *A61B 8/488* (2013.01); *A61B 8/06* (2013.01); *A61B 8/461* (2013.01); *G01S 7/52046* (2013.01); *G06T 5/009* (2013.01); *G06T 7/0012* (2013.01); *G06T 11/006* (2013.01); *G06T 2207/10024* (2013.01); *G06T 2207/10132* (2013.01); *G06T 2207/20056* (2013.01); *G06T 2207/20208* (2013.01); *G06T 2207/30048* (2013.01); *G06T 2207/30104* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 5,961,462 A | 10/1999 | Loupas et al. | |
| 6,221,020 B1 * | 4/2001 | Lysyansky | A61B 8/06 600/453 |
| 6,577,967 B2 * | 6/2003 | Mo | G01S 7/52026 702/76 |
| 6,663,566 B2 | 12/2003 | Pan et al. | |
| 6,733,454 B1 * | 5/2004 | Bakircioglu | A61B 8/06 600/453 |
| 7,288,068 B2 * | 10/2007 | Bakircioglu | A61B 8/06 600/455 |
| 7,578,792 B2 * | 8/2009 | Lee | A61B 8/06 600/437 |
| 7,627,386 B2 * | 12/2009 | Mo | A61B 8/00 600/437 |

(Continued)

*Primary Examiner* — Delomia L Gilliard

(57) ABSTRACT

In spectral Doppler imaging, a high PRF is used independent of the velocity scale. The adjustment is then of the velocity scale. By optimizing the velocity scale independent of the high PRF in an on-going or automated basis, user activation may be avoided and/or interruption to reconfigure for an altered PRF may be avoided. The acquired data may be stored, allowing for past data to be processed again when a new velocity scale or other setting is selected. The resulting spectral Doppler image may continue to display spectra over time without a gap or without premature loss of spectra due to reconfiguring.

20 Claims, 3 Drawing Sheets

(56) References Cited

U.S. PATENT DOCUMENTS

| | | | |
|---|---|---|---|
| 8,435,182 B1* | 5/2013 | Tamura | G01S 15/8986 600/437 |
| 2003/0045797 A1* | 3/2003 | Christopher | G01S 7/52026 600/453 |
| 2003/0158484 A1* | 8/2003 | Pan | G01S 15/8981 600/453 |
| 2005/0080329 A1* | 4/2005 | Uchibori | A61B 8/06 600/407 |
| 2007/0038083 A1* | 2/2007 | Srinivasan | A61B 8/06 600/437 |
| 2007/0161896 A1* | 7/2007 | Adachi | B06B 1/0292 600/437 |
| 2007/0161898 A1 | 7/2007 | Hao et al. | |
| 2008/0194957 A1* | 8/2008 | Hoctor | A61B 8/483 600/443 |
| 2009/0062654 A1* | 3/2009 | Zhang | A61B 8/06 600/455 |
| 2009/0171204 A1* | 7/2009 | Shin | G01S 7/52034 600/441 |
| 2010/0022884 A1* | 1/2010 | Ustuner | A61B 8/06 600/453 |
| 2012/0215110 A1* | 8/2012 | Wilkening | A61B 8/488 600/453 |
| 2014/0018680 A1* | 1/2014 | Guracar | A61B 8/463 600/440 |

* cited by examiner

SPECTRAL DOPPLER IMAGING WITH INTERRUPTION AVOIDANCE

BACKGROUND

The present embodiments relate to spectral Doppler ultrasound. By transmitting a plurality of pulses (pulsed wave (PW)) or a continuous wave (CW) at a single gate location, a spectral Doppler response is generated in response to received echo signals. The frequency spectrum of the object's motion or flow for a single spatial region is estimated and displayed as a function of time. Spectral Doppler ultrasound imaging provides an image of spectra as velocity values (vertical axis) modulated by energy as a function of time (horizontal axis) for a gate location. The spectra may be used for studying fluid flow or tissue motion within a patient.

Sonographers frequently manually adjust Doppler gain, dynamic range, wall filter, persistence, temporal resolution, or other parameters of the spectral Doppler imaging. Some adjustments, such as the pulse repetition frequency (PRF) to control aliasing, require a system reconfiguration. During or because of the reconfiguration, the scanning is interrupted, resulting in a loss of previously acquired data and starting over of the spectral imaging. While the adjustments may be automated, the automation still results in an interruption in the workflow to activate and/or during reconfiguration to acquire the data for the adjusted PRF. Even after optimal settings are applied, the display trace (image of spectra) is either broken up (temporal gap for which no spectra are provided) or prior data from the previous PRF is removed from the image (start the spectral strip over).

BRIEF SUMMARY

By way of introduction, the preferred embodiments described below include methods, systems, computer readable media, and instructions for spectral Doppler imaging. Rather than adjust the PRF, a high PRF is used. The adjustment is then of the velocity scale. By optimizing the velocity scale independent of the high PRF in an on-going or automated basis, user activation may be avoided and/or interruption to reconfigure for an altered PRF may be avoided. The acquired data may be stored, allowing for past data to be processed again when a new velocity scale or other setting is selected. The resulting spectral Doppler image may continue to display spectra over time without a gap or without premature loss of spectra due to reconfiguring.

In a first aspect, a method is provided for spectral Doppler imaging. A transducer transmits ultrasound energy to a Doppler gate location at a highest or higher pulse repetition frequency allowable by roundtrip travel of the ultrasound energy between the transducer and the Doppler gate location. The responses to the transmitting over time are stored. A first velocity scale is calculated from at least one of the responses to the transmitting. The first velocity scale is less than or equal to the pulse repetition frequency. First spectra are estimated over time for the Doppler gate location. The estimation based on the responses, uses the first velocity scale. A first image of the first spectra with the first velocity scale is displayed. The first image represents a first range of times. Later, a second velocity scale is calculated from at least another one of the responses to the transmitting. The second velocity scale is different than the first velocity scale. Second spectra over time are estimated for the Doppler gate location. The estimation of the second spectra based on the responses, uses the second velocity scale. A second image of the second spectra with the second velocity scale is displayed. The second spectra includes spectra from times within the first range of times also represented in the first image.

In a second aspect, a non-transitory computer readable storage medium has stored therein data representing instructions executable by a programmed processor for spectral Doppler imaging. The storage medium includes instructions for storing beamformed samples acquired at a first rate, determining different display scales over time, the different display scales avoiding aliasing based on the beamformed samples, the display scales less than the first rate, and generating a spectral Doppler strip using the different display scales without altering the first rate.

In a third aspect, a system is provided for spectral Doppler imaging. A transmit beamformer is configured to transmit acoustic energy to a Doppler gate in an ongoing manner. A receive beamformer is configured to sample acoustic echoes from the Doppler gate and in response to the acoustic energy. A spectral Doppler processor is configured to estimate spectra from the samples of the acoustic echoes for the Doppler gate. The spectra estimated from the samples use different settings of parameters at different times while representing overlapping times. A display is configured to display the spectra.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The workflow in Doppler mode in medical ultrasound is improved. Doppler parameters are optimized regularly, upon trigger, or continuously without the need to reconfigure the system. By acquiring the Doppler data at a highest possible PRF, there is no need to reconfigure the system due to a change in the Doppler parameters. For example, the acquired Doppler data is stored and processed at a display PRF or velocity scale that is free of aliasing and optimal for display. As the optimization indicates use of a different velocity scale, the data already acquired at the highest PRF may be reprocessed using the new velocity scale. Any interruption in the trace display may be eliminated by reprocessing the whole trace at the new settings. By eliminating button pushing and waiting time for reconfiguration, a continuous trace is produced despite change in the velocity scale. There is no need for the user to interrupt their workflow and no loss of data from changing the spectral trace.

Figure 1:
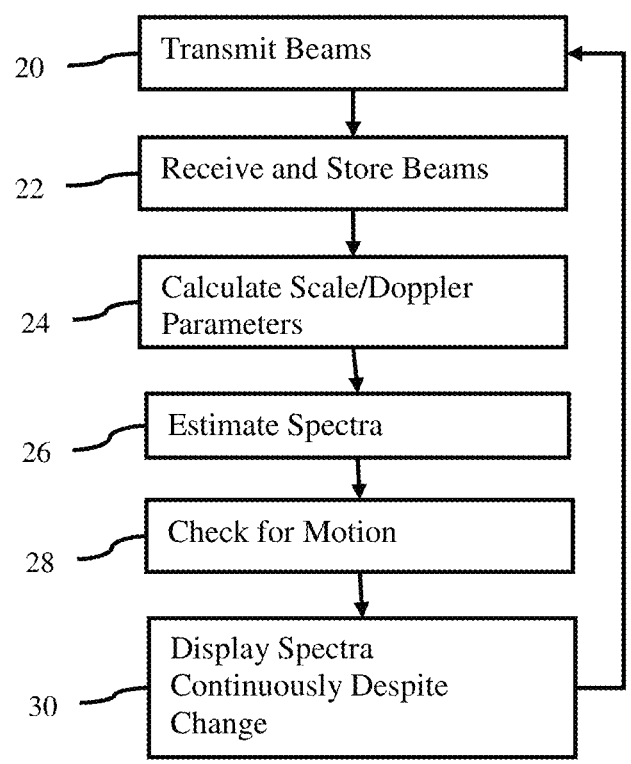
FIG. 1 is a flow chart diagram of one embodiment of a method for spectral Doppler imaging.

FIG. 1 shows a method for spectral Doppler imaging. The spectral Doppler imaging is optimized with a velocity scale set to avoid aliasing. The velocity scale may vary over time without reconfiguring the scanning or without changing the transmit and reception based on the different velocity scale.

Figure 5:
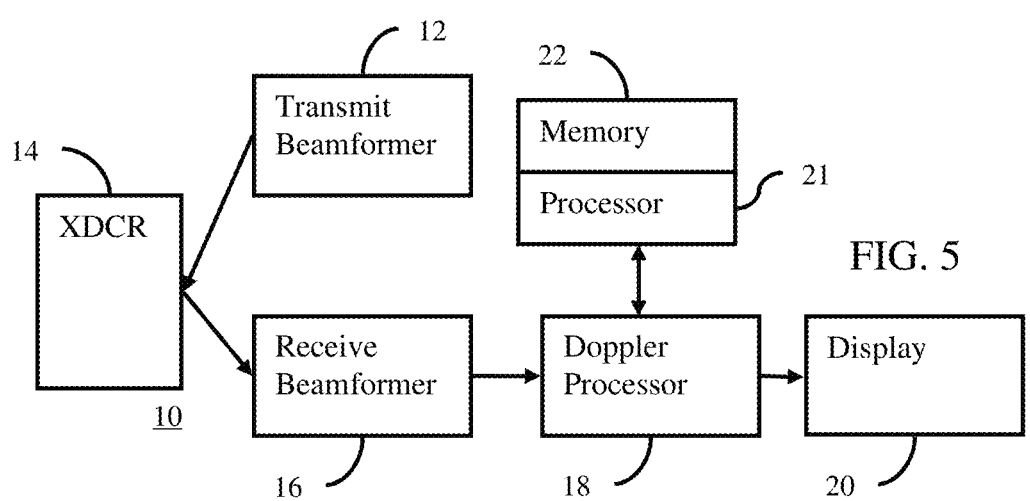
FIG. 5 is a block diagram of one embodiment of a system for enhancing spectral Doppler imaging.

The method is implemented by the system 10 of FIG. 5 or a different system. A processor controls and/or performs the acts. One or more acts may be performed through interaction with a user. Other acts or all the acts may be performed automatically by a processor without user input other than initial activation or gate location determination.

The acts are performed in the order shown, but other orders are possible. For example, act 28 is performed before act 24 or after act 30.

Additional, different, or fewer acts may be provided. For example, act 28 is not performed. In yet another example, acts for filtering, processing, maximum velocity determination over time, or other spectral Doppler functions are provided.

The method is implemented for pulsed wave (PW) or continuous wave (CW) spectral Doppler. "Doppler" is used to express spectral processing in general. Other spectral processes using ultrasound samples from different times may be used. In PW, a gate location is sampled using pulse wave (e.g., 1-50 cycles) transmissions interleaved with echo reception. PW may interleave with other modes of imaging, such as B-mode or flow-mode. In CW, a continuous wave (e.g., hundreds or thousands of cycles) is transmitted to the gate location, and echoes are received while transmitting.

For spectral Doppler imaging, the sample gate or spectral Doppler gate is positioned. For example, a B-mode and/or flow-mode scan is performed. The user indicates a gate location on the resulting image. In other examples, the gate is automatically positioned, such as at a location of greatest Doppler velocity or energy determined from flow-mode data.

In act 20, a transducer transmits a plurality of beams of acoustic energy. The acoustic or ultrasound energy of each transmission is focused at or near the gate location. The focus results in generation of a transmit beam. A sequence of transmissions is performed. The repetition allows reception of sufficient samples to perform spectral analysis. Any number, such as 3-20, of transmit beams are transmitted so that a spectrum of the response from the Doppler gate may be estimated.

By performing additional transmissions, additional information is obtained for estimating spectra at other times. A given response to a given beam may be used for different spectra, such as where a moving window of received responses is used to generate each spectrum.

The transmissions occur at a set or higher PRF allowable by roundtrip travel of the ultrasound energy between the transducer and the Doppler gate location. The ultrasound energy propagates from the elements of the transducer to the gate location, and echoes return to the elements. This roundtrip travel time plus a reverberation reduction period (e.g., ½ the roundtrip travel time) is a highest or set PRF in Doppler imaging. A higher PRF may be used, such as where the reverberation reduction time is reduced. An even higher PRF may be used, such as in CW or where PW transmissions are performed with a subsequent transmission occurring before echoes from the previous transmission are fully or completely received.

The set or higher PRF may account for interleaving with other modes of scanning. The set or higher PRF is determined for the spectral Doppler transmissions or blocks of time during which transmissions for other modes are not occurring. The interleaved transmissions from other modes may reduce the overall PRF achieved, but during the transmissions from the spectral Doppler mode alone, the set or higher PRF is used. Alternatively, the set or higher PRF is a repetition frequency of the spectral Doppler transmissions as reduced to provide for interleaving for other modes of imaging.

By acquiring at the set or higher PRF allowable by roundtrip travel time with any reverberation reduction, the PRF of the transmissions is more likely to oversample given the velocities of the flow or tissue at the gate location. Rather than calculating the amount of oversampling and reducing the PRF of the transmissions, the oversampling is allowed to continue. In some embodiments, the set or higher PRF may still result in aliasing.

In act 22, the transducer receives acoustic echoes. The echoes are received in response to the transmissions of the acoustic energy. A receive beamformer samples the echoes to acquire received signals for the gate location. Receive beams are formed by focusing the received signals to coherently combine data representing the gate location. This combined data representing the gate location are beamformed signals.

The receive operation occurs repetitively in response to the repetitive transmissions. Beamformed samples from the gate location at different times are received. Samples for the same location are acquired over time. For spectral analysis, an ensemble of samples from a same location is acquired, such as five to twenty samples for each spectrum. The samples may be obtained in an ongoing manner such that a moving window (e.g., ensemble or flow sample count) with any step size (e.g., every sample or every third sample) is used to estimate a spectrum.

These responses (e.g., beamformed samples or channel data used for beamforming) are stored in a memory, such as a main memory, corner turning memory, or CINE. The responses to the spectral Doppler transmissions are stored. This raw Doppler data prior to estimation is stored in an ongoing manner, such as storing the beamformed samples as acquired at a rate at the set or higher PRF.

The storage may be a first-in, first-out or other storage format. For example, the beamformed samples used to generate a currently displayed spectral Doppler image are stored. The image represents spectra for the gate location over a range of times. The responses used to estimate the spectrum for each time in the range are stored. As the spectrum is removed from the spectral Doppler image due to a new spectrum being added for the current time, the responses used only in the now non-imaged spectra are removed. The responses used for the currently displayed trace are stored. Alternatively, a greater or lesser number of responses are stored, such as only storing responses for the most recent fraction of all of the displayed spectra or storing responses for an amount of time after replacement of a spectrum.

Figure 2:
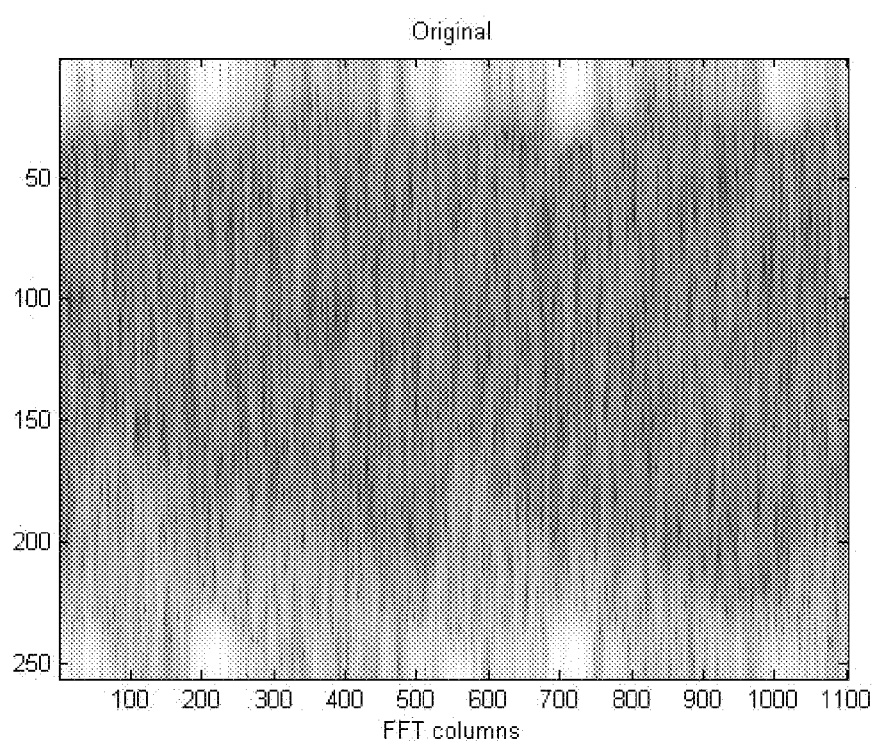
FIG. 2 is an example spectral Doppler image.

In act 24, a processor calculates a velocity scale. The velocity scale is limited by the set or higher PRF. However, excess range above the level of aliasing may result in less than all of the display field for the spectral Doppler image being used by velocities representing the tissue or flow. FIG. 2 shows an example spectral Doppler image where most (e.g., more than ¾) of the vertical range of velocities are associated with signal. If the set or higher PRF were used as the velocity scale, then the signal may be in less of the vertical space. The velocity scale is optimized to use the dynamic range available without aliasing while maximizing or using most of the vertical range.

The velocity scale is less than the PRF for the transmissions of act 20, but may be equal to the PRF. For example, the PRF is 10 kHz and the velocity scale is 1 kHz. Doppler responses are acquired at a highest PRF allowable by roundtrip travel or a higher PRF. These responses are then used to calculate optimal Doppler display scale, baseline and/or other processing parameters.

Since aliasing defines, in part, the desired velocity scale, the responses are used to calculate the velocity scale. Any metric, such as the mean velocity or peak velocity, may be used to calculate the velocity scale. The responses are used to estimate a spectrum or spectra over time, such as over one or more heart cycles. In one embodiment, the maximum positive, maximum negative, or both velocities from the flow or tissue in the spectrum or spectra is identified. The absolute value of the maximum indicates the velocity scale or range to avoid aliasing for unidirectional flow. An absolute difference between the negative and positive maximum peaks indicates the velocity scale or range to avoid aliasing for bidirectional flow. The scale may be set to the maximum or be the maximum as increased by a factor (e.g., constant, percentage, or ratio) to provide tolerance.

The metric is continuously, periodically, or occasionally calculated from the raw data (e.g., responses). The optimal display PRF (e.g., velocity scale) and/or baseline are determined from the metric such that the display window utilization (e.g., spectrum filling up a majority or at least ¾ of vertical space) is provided while avoiding aliasing.

Once the velocity scale is calculated, the spectral Doppler image may be generated using the velocity scale. Velocities for the image are estimated using the velocity scale. Any number of spectra may be estimated at a calculated or optimized velocity scale.

Other parameters may be calculated. The processor may determine settings for a baseline, a wall filter, persistence, inversion, gain, or combinations thereof as a function of the responses. For example, a baseline or mid value for the velocities, a wall filter for the range of velocities (e.g., altering cut-off frequency based on range of velocities), amount of persistence filtering, and/or which velocities (e.g., positive or negative) are displayed on which side of the baseline (e.g., arterial flow on top) are set. These settings are based on the responses, such as the range of velocities determined from the responses. In alternative embodiments, any one or more (e.g., all but velocity scale) are set by or overridden by the user. A user interface is operated to input the value or values of any of the parameters, such as replacing a computed or automatically determined value with a value input by the user.

Figure 3:
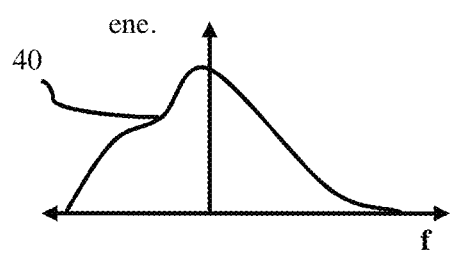
FIG. 3 is a graphical representation of an example spectrum.

In act 26, the processor estimates one or more spectra from the responses. A spectrum is estimated for the Doppler gate location. The spectrum is estimated by applying a Fourier transform, wavelet transform, or Wigner-Ville distribution to the sequence of ultrasound responses. Any transform may be applied to determine the spectrum. As shown in FIG. 3, the spectrum 40 represents energy as a function of frequency. Frequency has a known relationship to velocity, so expression in terms of frequency provides velocity and expression in terms of velocity provides frequency.

The spectrum is estimated using the velocity scale. The signal from the fluid or tissue is over a range of positive and negative velocities. The range used in the estimation is the velocity scale. Any velocities beyond the velocity scale wrap around or are aliased. By optimizing or calculating the velocity scale based on previous responses, velocities estimated for subsequent responses in a same gate location and examination are likely to not be aliased, at least in a short period. The spectrum provides energy as a function of frequency over the range of frequencies set by the velocity scale.

The spectrum is estimated from the ultrasound responses in the sequence from the Doppler gate location. The spectrum corresponds to a period in which the samples were acquired. The spectrum represents a time or the period. A sequence of spectra represents the Doppler gate location at different times. Other spectra may be estimated for other periods or different times corresponding to different periods or ensembles of acquisition. The periods may overlap, such as when using a moving window with a step size less than the ensemble period, or may be unique.

Figure 4:
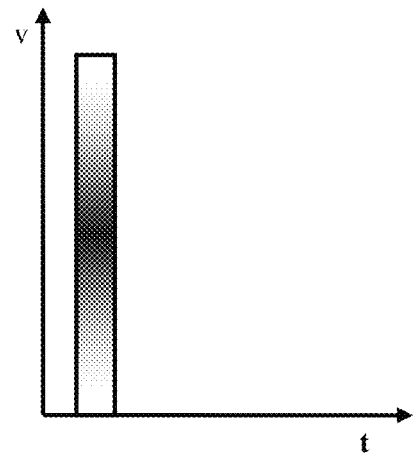
FIG. 4 is a graphical representation of an example spectrum with velocity modulated by energy mapped to a y-axis for a time and an example boundary.

FIG. 2 shows a spectral strip of spectra for a same location over time. The spectrum for a given time in a spectral strip is mapped with velocity on the horizontal axis and energy modulating the intensity, as shown by the graphical representation of the spectrum of FIG. 4. Other mapping may be used.

The acquisition of samples and estimating for a different period are repeated to provide spectra over time. For a spectral strip, the process and corresponding repetition is on-going or occurs multiple times.

In act 34, the processor generates an image on a display. The image is a function of the spectra, such as shown in FIG. 2. The spectrum or series of spectra may be used to generate a spectral strip. The spectral strip is displayed for the Doppler gate. Filtering may be applied to smooth the spectra along the time and/or frequency dimensions or over energy. The spectral strip shows the frequency modulated by energy as a function of time. Any now known or later developed spectral strip mapping may be used, such as gray scale mapping with the intensity representing energy. The energies modulate the pixels. The gray scale or color is mapped from the energy values. The displayed image may be a function of a single spectrum or of multiple spectra.

In one embodiment, the spectral strip is displayed with a spatial image, such as a one-dimensional M-mode, two-dimensional B-mode, two-dimensional F-mode (flow mode), or combination thereof image. The location of the gate may be indicated graphically in the image, such as represented by a circle in the region of interest of the field of view. For example, text, color, symbol, or other indicator shows the location for the range gate corresponding to the spectral strip. Alternatively, the spectral strip is displayed without imaging from another mode.

The spectral strip of the image includes the one or more spectra estimated with the calculated velocity scale. The velocity scale defines a vertical range on the spectral strip. As additional responses are acquired, the resulting spectra are added to the spectral strip, such as adding the spectra to a right side of the strip, shifting the remaining spectra one temporal step to the left, and removing the leftmost spectral strip. Other update or scrolling of the spectral strip may be used.

As represented by the feedback from act 30 to act 20, the transmission for the spectral Doppler imaging, resulting reception and storage of responsive samples, estimation of spectra, and display repeats. This repetition continues the update of the spectral strip.

The calculation of the velocity scale or other Doppler imaging parameters may also be repeated. The repetition of the calculation occurs continuously or during each repetition of spectrum estimation. Alternatively, the calculation is repeated less than every repetition of spectrum estimation. For example, the calculation is performed in response to user activation (e.g., depressing a button for automatic spectral strip optimization). As another example, the calculation is performed in response to an end-of-trace event, such as once spectra for the entire range of time represented in the spectral strip are estimated. In yet another example, a cardiac trigger from an ECG or ultrasound derived heart cycle signal is used (e.g., trigger every R-wave). In another example, a periodic trigger, such as every 5 seconds, is used. Other trigger events may be used to synchronize the automatic reprocessing for velocity scale or other parameters. By performing the calculation continuously or at other repetition in real-time during scanning and imaging in the background without user action, workflow interruption may be avoided.

The use of the repeated calculation may be limited. In addition to or as an alternative to providing re-calculation at specific triggers rather than continuously, the velocity scale may be changed only where the difference between the previous velocity scale and re-calculated velocity scale is sufficiently different (e.g., 25% change). Alternatively, other limits or no limits on the use of the recalculated velocity scale are provided.

Since the calculation repetition is performed after a previous calculation, the later calculation has different or additional responses available. As a result of being based on different group of responses, the later calculated velocity scale may be different than the earlier calculated velocity scale. The later calculation may be part of on-going (e.g., periodic or triggered) calculation to monitor the responses and adjust the velocity scale without user activation. With or without user activation, different display PRF or velocity scales are determined at different times. A scale that may avoid aliasing based on one set of responses may alias if used for another set of responses. Alternatively, a velocity scale that may optimize vertical spacing of the signal or dynamic range for one set of responses may be less optimal (e.g., use less) of the vertical spacing for another set of responses. The calculation is predictive of the velocity scale likely to be optimal for subsequent responses, but repeated calculation may allow the prediction to be adjusted for current responses.

In the repetition of act 26, spectra are estimated using the subsequent, adjusted, updated, or re-calculated velocity scale. As subsequent responses are received, the spectra estimated from the subsequent responses use the different or changed velocity scale.

Since the velocity scale defines the vertical extent of the spectral strip, the vertical dynamic range or scaling changes with the change in the velocity scale. In one embodiment, the spectral strip continues with spectra with a different dynamic ranged added on to previous spectra. In another embodiment, the previously stored responses are used to estimate replacement spectra for previous times. A given spectral strip represents spectral response over an immediate period from the past to the current. When the velocity scale changes, at least some of the past (e.g., all but the spectrum being scrolled off) spectra are estimated again, but with the new velocity scale. If the optimal display PRF differs from the currently used display PRF, the system automatically reprocesses the stored raw data at the current optimal display PRF. The spectra of the spectral strip, including spectra for periods previously displayed or representing periods for responses prior to the change in the velocity scale, are replaced with spectra representing the same times but estimated with the different or updated velocity scale.

The use of the set or higher PRF provides samples at a rate likely to be usable with any number of different velocity scales. The acquisition of responses at this high rate may result in unneeded scanning for the spectral strip, but allows for change in the velocity scale used in estimation without having to reconfigure the transmitting. As a result, the stored responses are likely to provide sufficient information to allow repetition of the estimation for the same period but with a different velocity scale. The PRF of the transmissions is not altered, but remains constant despite the change in the velocity scale.

In the repetition of the display of act 30, all or some of the spectra in the spectral strip are based on the current or updated velocity scale. Where the previously acquired responses are used again to estimate but with a different velocity scale, all or most of the spectra in the strip are replaced with updated estimates. The spectrum of the most recent time from the previous strip is replaced with a spectrum estimated from the responses for that most recent time. As new responses are acquired or based on subsequently acquired responses, spectra are added for later times. Spectra from times within the range of times represented in a previous spectral strip are replaced, providing a continuity in the strip without interruption to alter the transmitting. The replacement strip includes spectra representing some of the same times as the pervious strip, but estimated with the different velocity scale.

Any number of spectra may be replaced so that the spectral strip displayed at a given time has the same velocity scale for all or most of the spectra. For example, all spectra to be displayed, even for past times, are replaced. In another example, at least five spectra from the five most temporally immediate times are replaced.

From the user's perspective, there is no interruption to acquisition and no loss of data. The spectral strip may jump or change due to the different velocity scale, but the periods represented by the strip appear to scroll regularly and without a gap due to a change in transmission PRF. The only interruption, if any, is to re-draw (e.g., re-estimate) the Doppler trace at the new display PRF. This redrawing may not result in any temporal gap in the strip. The image is replaced while maintaining spectral representation of at least some of the past times represented in a previous spectral Doppler strip.

In act 28, the processor detects motion of the patient relative to the transducer. B-mode data, the spectral Doppler data (e.g., responses and/or spectra), or other data is analyzed for indications of motion other than heart or expected physiological motion. For example, deviation of an energy weighted average velocity by a threshold amount away from a baseline indicates motion. As another example, an amount of decorrelation of data or large offset for a highest correlation between images of different times indicates motion. In alternative embodiments, a motion sensor is placed on the transducer. The amount of motion is determined from the motion sensor.

If the amount of motion is below a threshold, then the repetition to update the spectral strip and/or on-going calculation of act 24 continues. If the amount of motion is above the threshold, then the repetition of the acts and/or calculation of act 24 is ceased. The spectral strip is not updated for one or more time periods, causing a temporal gap until the motion falls below the threshold. Alternatively, the spectral strip is updated but the velocity scale is maintained constant during the motion.

FIG. 5 shows a system 10 for spectral Doppler imaging. The system 10 is a medical diagnostic ultrasound imaging system, but other imaging systems may be used, such as a workstation. The system 10 acquires responses at a gate location at a high rate (e.g., highest PRF allowed given interleaving for other modes, reverberation reduction, and travel time back and forth between the transducer and the gate location), allowing use of different or varying velocity scales without interrupting the acquisition. The velocity scale may be changed while still representing past times in the spectral strip since responses are collected at the high rate. The velocity scale may be optimized automatically without user changing the velocity scale and without interruption (e.g., without a temporal gap in the strip and without starting the strip over) in the imaging of spectra over time.

The system 10 includes a transmit beamformer 12, a transducer 14, a receive beamformer 16, a Doppler processor 18, a display 20, a processor 21, and a memory 22. Additional, different or fewer components may be provided, such as the system 10 without the front-end beamformers 12, 16 and transducer 14 or the system 10 with a scan converter. The Doppler processor 18 and processor 21 may be combined into one device acting as both processors 18, 21, or additional processors for sequential or parallel processing may be used.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some components in common. Operating together or alone, the transmit and receive beamformers 12, 16 form beams of acoustic energy for sampling a gate location and/or scanning a one, two, or three-dimensional region.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates transmit waveform envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. Alternatively, the transmit beamformer 12 generates continuous waves for CW imaging. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, or combinations thereof.

The transmit beamformer 12 is configured to transmit a sequence of transmit beams of ultrasound energy. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The acoustic energy is focused at the Doppler gate location, but may be focused elsewhere (e.g., the Doppler gate is along the scan line but not at the focus). The beam of acoustic energy is transmitted to the Doppler gate.

An ongoing sequence of transmit beams are generated at a PRF. The PRF determines the interval between temporally adjacent transmissions or transmit beams. The PRF may be low enough to have a period of no transmission not needed for travel time, interleaving with other imaging modes, and reverberation reduction. In one embodiment, the PRF is as rapid as possible given the travel time, interleaving, and reverberation reduction of ½ the travel time or less. The highest PRF allowed given the travel time, interleaving, and reverberation reduction is used. Higher PRF may be provided, such as by using less or not including reverberation reduction and/or not accounting for interleaving (e.g., PRF is of spectral Doppler transmissions only between any interleaving). Even higher PRF may be provided where ghosting is acceptable by transmitting a subsequent beam before echoes from the gate location of a previous transmit beam are received (i.e., PRF no limited by travel time).

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used.

The receive beamformer 16 is configured into a plurality of channels for receiving electrical signals representing echoes or acoustic energy impinging on the elements of the transducer 14. A channel from each of the elements of the receive aperture within the transducer 14 connects to an amplifier for applying apodization amplification. An analog-to-digital converter may digitize the amplified echo signal. The radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. The summer sums the relatively delayed and apodized channel information together to form a beam. Beamformed samples of echoes from the gate location are obtained.

In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

Beamforming parameters including a receive aperture (e.g., the number of elements and which elements used for receive processing), the apodization profile, a delay profile, a phase profile, imaging frequency, inverse coding, or combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated at the Doppler gate and in response to each transmit beam. Acoustic echoes are received by the transducer 14 in response to the transmitted acoustic energy. The echoes are converted into electrical signals by the transducer 14, and the receive beamformer 16 forms the receive beams from the electrical signals to generate samples representing the gate location. Given the ongoing transmit beams at the PRF, samples are generated in an ongoing manner as well. Responses over time are acquired.

The Doppler processor 18 is a spectral Doppler processor. Other imaging detectors may be included, such as a B-mode and flow-mode processors. In one embodiment, the Doppler processor 18 is a digital signal processor or other device for applying a transform to the receive beam sample data. A sequence of transmit and receive events is performed over a period. A buffer (e.g., corner turning memory) or the memory 22 stores the receive beamformed data from each transmit and receive event. A wall filter, such as a programmable filter for distinguishing between tissue and fluid motion, may filter the samples prior to application of the transform. Any number of transmit and receive events may be used for determining a spectrum, such as three or more. The Doppler processor 18 estimates a spectrum for the gate location. By applying a discrete or fast Fourier transform, or other transform, to the ultrasound samples for the same spatial location, the spectrum representing the response from the location is determined. A histogram or data representing the energy level at different frequencies for the period to acquire the samples is obtained. Velocity may be determined from the frequency or frequency is used without conversion to velocity.

By repeating the process, the Doppler processor 18 may obtain different spectra for a given location at different times. Overlapping data may be used, such as calculating each spectrum with a moving window of selected ultrasound samples. Alternatively, each ultrasound sample is used for a single period and corresponding spectrum.

The Doppler processor 18 applies the transform for a range of frequencies. The range of frequencies or velocity scale limits the positive and negative velocities resulting from the estimation. Any of various velocity scales may be used, up to and including a velocity scale equal to the transmission PRF. The spectra are estimated using a given velocity scale. Different velocity scales may be used at different times, such as where the samples have different characteristics. The spectra are estimated using a same or different settings for other parameters (e.g., wall filter, inversion, baseline, or persistence) at different times.

The spectra for the same times may be estimated using different velocity scales. When a parameter is changed, the change may be applied to the current and future estimation of spectra as well as to past estimation. The stored samples are used to estimate spectra for past times given the new settings. For overlapping times between a strip using one velocity scale and a strip using a different velocity scale, the Doppler processor 18 re-estimates the spectra. Any amount of overlap may be provided upon a change in a setting of a parameter.

The processor 21 may be part of the Doppler processor 18 or a separate processor. The processor 21, Doppler processor 18, or both processors 18, 21 are used for estimation and/or to control the imaging and/or system 10. The processor 21 is a general processor, control processor, digital signal processor, application specific integrated circuit, field programmable gate array, graphics processing unit, analog circuit, digital circuit, combinations thereof or other now known or later developed device for processing.

The processor 21 is configured by hardware, software, or both to perform and/or cause performance of various acts, such as the acts discussed above for FIG. 1. The processor 21 is configured, as part of or in communication with the Doppler processor 18, to determine the settings of parameters used by the Doppler processor 18 and the beamformers 12, 16. The processor 21 sets the PRF for the beamformers 12, 16 given a location of a Doppler gate relative to the transducer 14. The highest PRF as limited by interleaving for other modes, travel time, and/or reverberation reduction is used. A higher PRF may be used.

The processor 21 optimizes the Doppler imaging parameters based on the received samples. To avoid aliasing, the velocity scale is set to include the frequencies or velocities represented in the samples. Given the high PRF, no aliasing is likely. Thus, the velocity scale may be set less than the PRF while still avoiding aliasing. To provide more desirable dynamic range, the velocity scale is set to avoid aliasing, but not by much (e.g., within 25%). Over time, the range over which aliasing occurs may change, so the processor 21 may re-calculate the velocity scale at later times. The processor 21 controls the Doppler processor 18 to operate based on the re-calculated parameters for those later times.

The processor 21 generates or causes the Doppler processor 18 to generate the spectral strip. As the acquisition and estimation continue, spectra are added to the strip and old spectra are removed in a first-in, first-out scroll. Where one or more settings of a parameter change (e.g., velocity scale is changed), the processor 21 causes re-estimation from stored samples of spectra currently represented in the strip. The previous strip is replaced with a new strip using the re-calculated parameters, but maintaining the scrolling and temporal representation without interruption.

The processor 21 operates automatically. The user activates the spectral Doppler mode and may position the gate. The optimization of parameters occurs without further user input and/or without user input of the values for one or more of the parameters (e.g., without user input of the velocity scale). In alternative embodiments, the user inputs the setting of the parameter. The processor 21 causes re-estimation using the new settings to avoid interruption.

Additional processes, such as filtering, interpolation, and/or scan conversion, may be provided by the Doppler processor 18, the processor 21, or another device. The spectra are prepared and formatted for display. For example, the Doppler processor 18 generates display values as a function of the spectra estimated for the Doppler gate location. Display values include intensity or other values to be converted for display (e.g., red, green, blue values) or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values are generated for a spectral strip display.

The display 18 is a CRT, monitor, LCD, plasma screen, projector or other now known or later developed display for displaying an image responsive to the spectra. For a grey scale spectral Doppler image, a range of velocities with each velocity modulated as a function of energy is provided as a function of time. A given spectrum indicates the velocity and energy information for a given time. The intensity of a given pixel or pixel region represents energy where velocity is provided on the vertical scale and time provided on the horizontal scale. Other image configurations may be provided, including colorized spectral Doppler images.

The memory 22 stores ultrasound samples for the range gate, estimated spectra, re-estimated spectra, settings (e.g., values) for parameters, image data, or other information. The memory 22 may store information from any stage of processing or used for generating a display. By storing samples for any currently displayed spectra, the samples are available for re-estimation using one or more different settings. To avoid interruption the spectral strip or limit interruption, the stored samples are used again to estimate given new or changed settings.

In one embodiment, the memory 22 is a non-transitory computer readable storage medium having stored therein data representing instructions executable by the programmed processor 18 and/or processor 21 for spectral Doppler imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts, or tasks are independent of the particular type of instructions set, storage media, processor, or processing strategy and may be performed by software, hardware, integrated circuits, firmware, micro code or the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for spectral Doppler imaging, the method comprising:
    transmitting, from a transducer, ultrasound energy to a Doppler gate location at a set or higher pulse repetition frequency allowable by roundtrip travel of the ultrasound energy between the transducer and the Doppler gate location;
    storing responses to the transmitting over time;
    calculating a first velocity scale from at least one of the responses to the transmitting, the first velocity scale less than or equal to the pulse repetition frequency;
    estimating from the responses, first spectra over time for the Doppler gate location, the estimating using the first velocity scale;
    displaying a first image of the first spectra with the first velocity scale, the first image representing a first range of times;
    later calculating a second velocity scale from at least another one of the responses to the transmitting, the second velocity scale different from the first velocity scale;
    estimating from the responses, second spectra over time for the Doppler gate location, the estimating of the second spectra using the second velocity scale; and
    displaying second image of the second spectra with the second velocity scale, the second spectra including spectra from times within the first range of times also represented in the first image.

2. The method of claim 1 wherein transmitting at the set or higher pulse repetition frequency comprises transmitting with the pulse repetition frequency being greater than allowable by the roundtrip travel.

3. The method of claim 1 wherein transmitting at the set pulse repetition frequency allowable by the roundtrip travel comprises transmitting with the set pulse repetition frequency allowable by roundtrip travel time with interleaving for B-mode scanning.

4. The method of claim 1 wherein storing the response comprises storing beamformed samples.

5. The method of claim 1 wherein calculating the first and second velocity scales comprises determining velocity peaks from the responses and setting the velocity scale based on the velocity peaks.

6. The method of claim 1 wherein calculating the first and second velocity scales comprises calculating the velocity scales to avoid aliasing while presenting a signal over a majority of vertical space of the first and second images.

7. The method of claim 1 wherein estimating the first and second spectra comprises applying a Fourier transform to the responses representing the Doppler gate location, the first and second spectra each comprising energy as a function of frequency over a range set by the respective velocity scale.

8. The method of claim 1 wherein displaying the first image comprises displaying a spectral Doppler strip updated as the responses from the transmitting are acquired.

9. The method of claim 8 wherein displaying the second image comprises replacing the first image while maintaining at least some of the past times representing in the spectral Doppler strip.

10. The method of claim 8 wherein displaying the second image comprises replacing the first image without altering the pulse repetition frequency and without interruption of the transmitting.

11. The method of claim 1 wherein later calculating the second velocity scale comprises calculating the second velocity scale from the responses occurring after the calculating of the first velocity scale.

12. The method of claim 1 wherein later calculating the second velocity scale comprises calculating in response to user activation, an end of trace event, or a cardiac trigger.

13. The method of claim 1 wherein later calculating the second velocity scale is part of on-going calculation to monitor the responses and adjust from the first velocity scale without user activation.

14. The method of claim 13 further comprising detecting motion of a patient relative to the transducer and ceasing the on-going calculation during the motion.

15. The method of claim 1 further comprising calculating a setting for a baseline, wall filter, persistence, inversion, or combinations thereof as a function of the responses.

16. In a non-transitory computer readable storage medium having stored therein data representing instructions executable by a programmed processor for spectral Doppler imaging, the storage medium comprising instructions for:
    storing beamformed samples acquired at a first rate;
    determining different display scales over time, the different display scales avoiding aliasing based on the beamformed samples, the display scales less than the first rate; and
    generating a spectral Doppler strip using the different displace scales without altering the first rate.

17. The non-transitory computer readable storage medium of claim 16 wherein storing comprises storing the beamformed samples as acquired with the first rate comprising a set or higher pulse repetition frequency allowing a roundtrip travel of acoustic energy from a transducer to a gate location.

18. The non-transitory computer readable storage medium of claim 16 wherein determining comprises determining without user adjustment of the display scale.

19. The non-transitory computer readable storage medium of claim 16 wherein generating the spectral Doppler strip comprises replacing a first strip representing spectra of a first time range including a current time using a first of the different display scales with a second strip representing spectra of a second time range including the current time and at least five previous times of the first time range, the second strip using a second of the different display scales for the spectra of the second time.

20. A system for spectral Doppler imaging, the system comprising:
    a transmit beamformer operable to transmit acoustic energy to a Doppler gate in an ongoing manner;
    a receive beamformer operable to sample acoustic echoes from the Doppler gate and in response to the acoustic energy;
    a spectral Doppler processor configured to estimate spectra from the samples of the acoustic echoes for the Doppler gate, the spectra estimated from the samples using different settings of parameters at different times while representing overlapping times; and
    a display configured to display the spectra.

* * * * *